(12) United States Patent
Gross et al.

(10) Patent No.: US 6,617,327 B2
(45) Date of Patent: Sep. 9, 2003

(54) ANTIDEPRESSANT AZAHETEROCYCLYLMETHYL DERIVATIVES OF 2,3-DIHYDRO-1,4-DIOXINO[2,3-F]QUINOXALINE

(75) Inventors: Jonathan L. Gross, Robbinsville, NJ (US); Gary P. Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/128,722

(22) Filed: Apr. 23, 2002

(65) Prior Publication Data

US 2002/0183329 A1 Dec. 5, 2002

Related U.S. Application Data

(60) Provisional application No. 60/286,438, filed on Apr. 26, 2001.

(51) Int. Cl.[7] .................. A61K 31/4985; C07D 491/04
(52) U.S. Cl. ........................................ 514/250; 544/345
(58) Field of Search ............................ 544/345; 514/250

(56) References Cited

U.S. PATENT DOCUMENTS

| 5,318,988 A | 6/1994 | Schohe-Loop et al. |
| 5,371,094 A | 12/1994 | Heine et al. |
| 5,741,789 A | 4/1998 | Hibschman et al. |
| 5,756,532 A | 5/1998 | Stack et al. |
| 5,869,490 A | 2/1999 | Stack |

FOREIGN PATENT DOCUMENTS

| EP | 0 771 800 A2 | 5/1997 |
| WO | WO 91/13872 | 9/1991 |
| WO | WO 97/23485 | 7/1997 |

OTHER PUBLICATIONS

Wyatt et al, Abstract for Cochrane Database of Systematic Reviews,CD001396 (2002).*
Martenyi et al. Abstract for Journal of Clinical Psychiatry, vol.63, p. 199–206 (Mar. 2002).*
Rushton et al. Abstract for Pediatrics, vol. 105,p. E82 (Jun. 2000).*
Sundstrom–Poromaa et al., Abstract for J. Psychosom. Obstet. Gynaecol., vol.21,p.205–211 (Dec. 2000).*
Robichaud et al in Annual Reports in Medicinal Chemistry, vol.35, p. 11–20 (2000).*

* cited by examiner

Primary Examiner—Emily Bernhardt
(74) Attorney, Agent, or Firm—Rebecca R. Barrett

(57) ABSTRACT

Compounds of the formula:

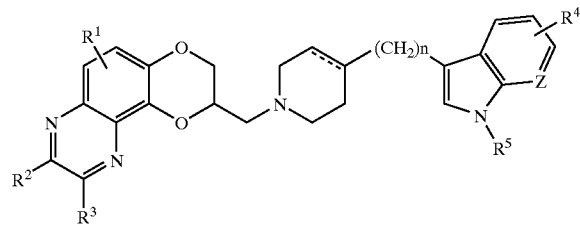

are useful for the treatment of depression and other diseases such as obsessive compulsive disorder, panic attacks, generalized anxiety disorder, social anxiety disorder, sexual dysfunction, eating disorders, obesity, addictive disorders caused by ethanol or cocaine abuse and related illnesses.

25 Claims, No Drawings

ANTIDEPRESSANT AZAHETEROCYCLYLMETHYL DERIVATIVES OF 2,3-DIHYDRO-1,4-DIOXINO[2,3-F]QUINOXALINE

This application claims priority from co-pending provisional application Ser. No. 60/286,438, filed on Apr. 26, 2001, the entire disclosure of which is hereby incorporated by reference.

BACKGROUND OF THE INVENTION

Major depression is a serious health problem affecting more than 5% of the population, with a life-time prevalence of 15–20%.

Selective serotonin reuptake inhibitors have produced significant success in treating depression and related illnesses and have become among the most prescribed drugs. They nonetheless have a slow onset of action, often taking several weeks to produce their full therapeutic effect. Furthermore, they are effective in fewer than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, 5-HT$_{1A}$ receptors, causing a decrease in serotonin release in major forebrain areas. This negative feedback limits the increment of synaptic serotonin that can be induced by antidepressants.

A 5-HT$_{1A}$ antagonist would limit the negative feedback and should improve the efficacy of the serotonin reuptake mechanism. (Perez, V., et al., *The Lancet*, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the 5-HT$_{1A}$ receptor.

DESCRIPTION OF THE INVENTION

In accordance with this invention, there is provided a group of novel compounds of the formula:

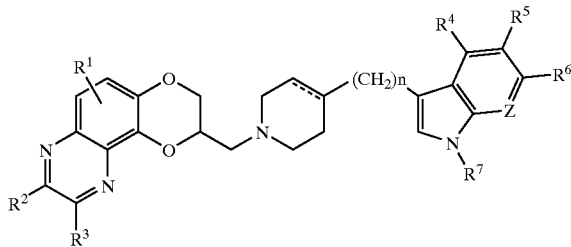

I wherein $R^1$, $R^4$, $R^5$, $R^6$ and $R^8$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ and $R^3$, are independently; hydrogen, alkyl of 1 to 6 carbon atoms, halogen, hydroxy, cyano or amino;

$R^7$ is hydrogen or alkyl of 1 to 6 carbon atoms;

the dotted line represents an optional double bond;

Z is $CR^8$ or N; and n is an integer 0, 1 or 2;

or a pharmaceutically acceptable salt thereof.

Of these compounds, the preferred members are those in which $R^1$ is hydrogen, hydroxy, halo, cyano, trifluoromethyl, alkyl of one to six carbon atoms or alkoxy of one to six carbon atoms. Still more preferred are compounds in which $R^1$ is hydrogen.

In other preferred embodiments $R^2$ is hydrogen, alkyl of one to six carbon atoms, amino, mono- or di-alkylamino in which each alkyl group has one to six carbon atoms. Still more preferred are compounds in which $R^2$ is hydrogen or lower alkyl.

$R^3$ is preferably hydrogen or alkyl of one to six carbon atoms. Still more preferred are compounds in which $R^3$ is hydrogen or lower alkyl.

In some embodiments of the present invention it is preferred that $R^2$ and $R^3$ are the same and are selected from hydrogen and lower alkyl.

$R^4$, $R^5$ and $R^6$ are preferably independently selected from hydrogen, hydroxy, halogen, cyano, carboxamido, alkyl of one to six carbon atoms, and alkoxy of one to six carbon atoms. $R^4$, $R^5$ and $R^6$ are more preferably independently selected from hydrogen and halogen.

$R^7$ is preferably hydrogen.

When Z is $CR^8$, then $R^8$ is hydrogen, hydroxy, halogen, cyano, carboxamido, alkyl of one to six carbon atoms, or alkoxy of one to six carbon atoms.

It is preferred in some embodiments of the invention that n is 0 or 1. Still more preferred is when n is 0.

In other preferred embodiments of the present invention $R^1$ is hydrogen, hydroxy, halo, cyano, trifluoromethyl, alkyl of one to six carbon atoms or alkoxy of one to six carbon atoms; $R^2$ is hydrogen, alkyl of one to six carbon atoms, amino, mono- or di-alkylamino in which each alkyl group has one to six carbon atoms; $R^3$ is hydrogen or alkyl of one to six carbon atoms; $R^4$, $R^5$ and $R^6$ are independently selected from hydrogen, hydroxy, halo, cyano, carboxamido, alkyl of one to six carbon atoms, or alkoxy of one to six carbon atoms; and n is an integer 0 or 1.

Most preferred are compounds in which $R^2$ and $R^3$ are the same and are hydrogen or alkyl of one to six carbon atoms, $R^4$, $R^5$ and $R^6$ are independently selected from hydrogen, halogen and cyano, $R^7$ is hydrogen, Z is $CR^8$, $R^8$ is preferably hydrogen, hydroxy, halo, cyano, carboxamido, alkyl of one to six carbon atoms or alkoxy of one to six carbon atoms, n is 0 and the dotted line represents a double bond.

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group RO—C(=O)— where R is an alkyl group of 1 to 5 carbon atoms.

Halogen (or halo) as used herein refers to chlorine, bromine, fluorine and iodine.

This invention relates to both the R and S stereoisomers of the amino-methyl-2,3-dihydro-1,4-dioxino[2,3-f]quinoxalines, as well as to mixtures of the R and S stereoisomers. Throughout this application, the name of the product of this invention, where the absolute configuration of the aminomethyl-2,3-dihydro-1,4-dioxino[2,3-f]quinoxalines is not indicated, is intended to embrace the individual R and S enantiomers as well as mixtures of the two. In some embodiments of the present invention the S stereoisomer is preferred.

Where a stereoisomer is preferred, it may in some embodiments be provided substantially free of the corresponding enantiomer. Thus, an enantiomer substantially free of the corresponding enantiomer refers to a compound which is isolated or separated via separation techniques or prepared free of the corresonding enantiomer. Substantially free, as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

It is further recognized that tautomers of the claimed compounds may exist for instance when R$^2$ or R$^3$ is OH, the compounds may exist in a number of tautomeric forms. The claims in the application, either for the title compounds or intermediates are intended to embrace individual tautomers, as well as mixtures thereof.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention include:

2-{[4-(5-fluoro-1H-indol-3-yl)-3,6-dihydro-1(2H)-pyridinyl]methyl}-2,3-dihydro[1,4]dioxino[2,3-f]quinoxaline;

2-{[4-(1H-indol-3-yl)-3,6-dihydro-1(2H)-pyridinyl]methyl}-2,3-dihydro-[1,4]dioxino[2,3-f]quinoxaline;

2-{[4-(1H-indol-3-yl)-3,6-dihydro-1(2H)-pyridinyl]methyl}-8,9-dimethyl-2,3-dihydro[1,4]dioxino[2,3-f]quinoxaline;

2-{[4-(5-fluoro-1H-indol-3-yl)-3,6-dihydro-1(2H)-pyridinyl]methyl}-8,9-dimethyl-2,3-dihydro[1,4]dioxino[2,3-f]quinoxaline;

8,9-diethyl-2-{[4-(1H-indol-3-yl)-3,6-dihydro-1(2H)-pyridinyl]methyl}-2,3-dihydro[1,4]dioxino[2,3-f]quinoxaline; and 8,9-diethyl-2-{[4-(5-fluoro-1H-indol-3-yl)-3,6-dihydro-1(2H)-pyridinyl]-methyl}-2,3-dihydro[1,4]dioxino[2,3-f]quinoxaline; and pharmaceutically acceptable salts thereof.

Novel intermediates are provided in some embodiments of the invention. Said intermediates have the formula

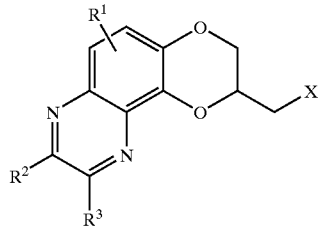

II wherein

R$^1$ hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

R$^2$ and R$^3$ are independently selected from hydrogen, alkyl of 1 to 6 carbon atoms, halogen, hydroxy, cyano and amino;

X is hydroxy, halogen, alkylsulfonate of 1 to 6 carbon atoms, trifluoromethanesulfonate or benzenesulfonate, in which the benzene ring is optionally substituted with halogen, nitro, trifluoromethyl, cyano, alkyl of 1 to 6 carbon atoms or alkoxy of 1 to 6 carbon atoms.

Compounds of Formula II are particularly useful in the preparation of compounds of Formula I. Preferred examples of compounds of Formula II include:

2,3-Dihydro[1,4]dioxino[2,3-f]quinoxalin-2-ylmethyl 4-methylbenzenesulfonate;

8,9-dimethyl-2,3-dihydro[1,4]dioxino[2,3-f]quinoxalin-2-yl]methyl 4-methylbenzenesulfonate; and 8,9-diethyl-2,3-dihydro[1,4]dioxino[2,3-f]-quinoxalin-2-ylmethyl 4-methylbenzenesulfonate.

The 2-azaheterocyclylmethyl-2,3-dihydro-1,4-dioxino[2,3-f]quinoxalines of the invention are prepared as illustrated in Schemes I–III. Specifically, the appropriately substituted nitroguaiacol (1) is alkylated with allyl bromide in the presence of a suitable base such as sodium hydride to produce (2) and then demethylated by a reagent such as sodium hydroxide. The resulting 4-nitro-2-allyloxyphenol (3) is then alkylated with glycidyl tosylate or an epihalohydrin in the presence of a base such as sodium hydride to produce (4) and heated in a high boiling solvent such as mesitylene or xylene to effect both rearrangement of the allyl group and cyclization of the dioxan ring. The resulting primary alcohol (5) is converted to the tosylate by reaction with p-toluenesulfonyl chloride in the presence of a tertiary amine or alternatively to a halide by reaction with carbon tetrabromide or carbon tetrachloride in combination with triphenylphosphine. The allyl side chain is then isomerized by treatment with catalytic bis-acetonitrile palladium (II) chloride in refluxing methylene

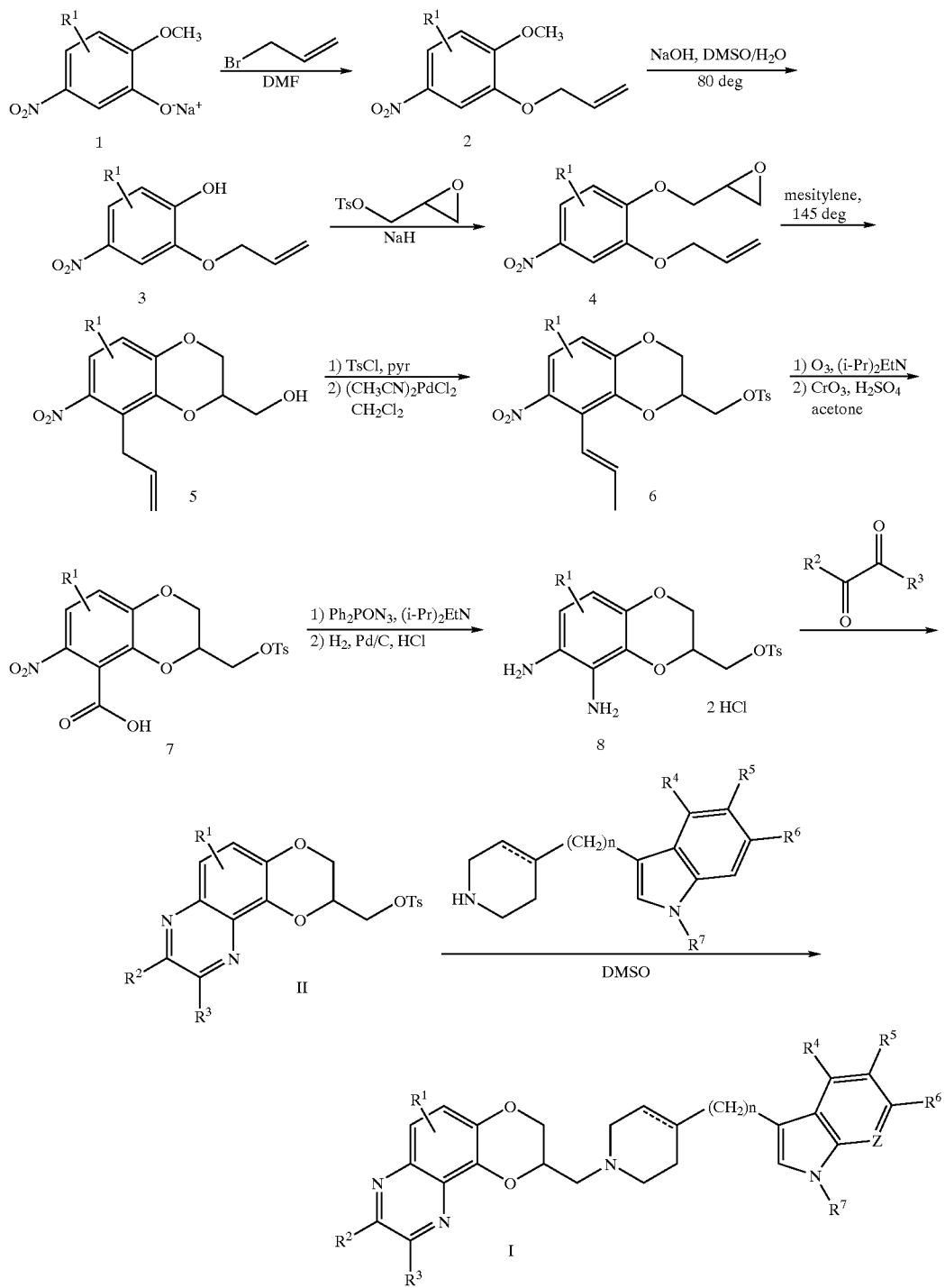

Scheme I chloride or benzene to produce (6) and cleaved to the corresponding o-nitrobenz-aldehyde by treatment with ozone followed by diisopropylethylamine or by catalytic osmium tetroxide in the presence of sodium periodate. The aldehyde is oxidized to the o-nitrobenzoic acid (8) by a suitable oxidant such as chromium trioxide (Jones' oxidation) or sodium chlorite and the acid converted to the o-nitroaniline with diphenylphosphoryl azide (DPPA) in the presence of a tertiary base such as diisopropylethylamine. Reduction of the resulting nitroaniline to the diamine (8) with hydrogen and palladium on carbon and cyclization by treatment with the appropriate dicarbonyl compound in some high boiling solvent such as dimethyl sulfoxide gives the title compounds of Formula I.

The o-nitrobenzaldehydes and the o-nitrobenzoic acids used in the chemistry described in Scheme I may be alternatively prepared as described in Scheme II. The appropriate mono-allylated catechol (10) is elaborated with glycidyl

Scheme II

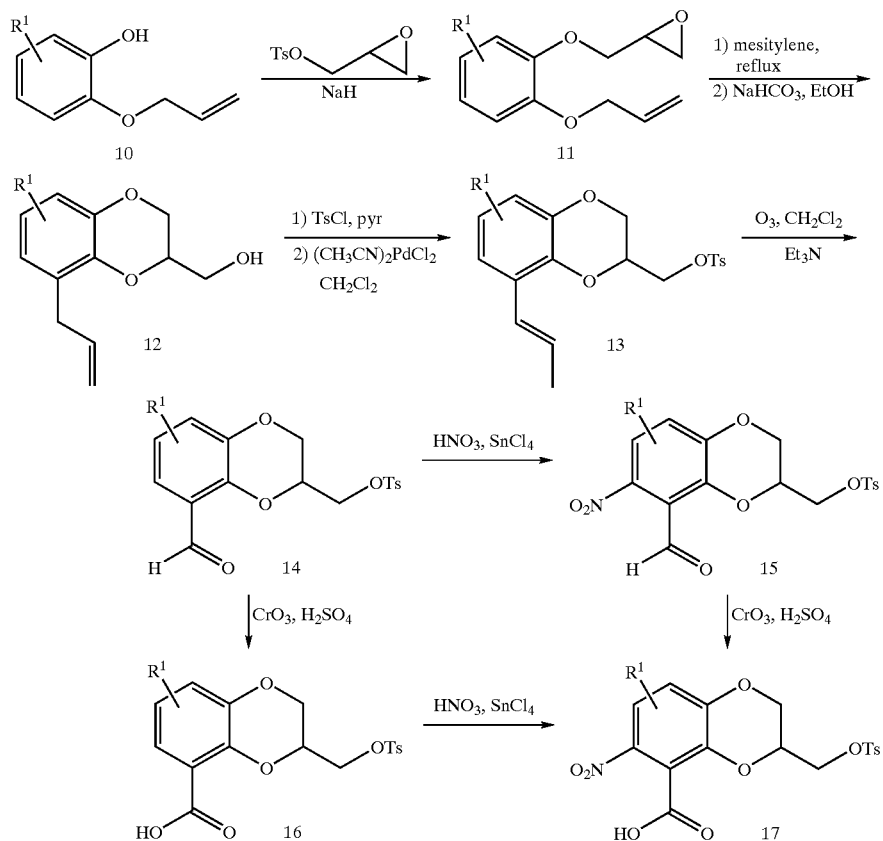

benzodioxan methanol (12) is effected by treatment with sodium bicarbonate in ethanol and the alcohol is converted to the tosylate or halide as described above. After rearrangement of the double bond by treatment with catalytic bis-acetonitrile palladium (II) chloride in refluxing methylene chloride to produce (13) and cleavage with ozone or osmium tetroxide/sodium periodate as described above, the resulting aldehyde (14) is regioselectively nitrated with a combination of nitric acid and tin (IV) chloride to produce (15). Alternatively, the aldehyde may be oxidized to the corresponding benzoic acid under Jones' conditions as described above to produce (16) and subsequently nitrated to produce the appropriate o-nitrobenzoic acid (17).

Compounds of the invention in which $R^2$ and $R^3$ are not identical may be prepared from assymetric dicarbonyl compounds as described above and the regioisomers separated by chromatography. They may alternatively be prepared from the o-nitroaniline described above as shown in Scheme III. The appropriately substituted o-nitroaniline (18) is deprotonated with a base such as sodium hydride and alkylated with a suitable α-haloketone or aldehyde, or an α-haloacetal or ketal to produce (19). The nitro group is then converted to an amine by hydrogenation over a catalyst such as palladium on carbon and cyclization effected with hydrochloric acid. A suitable oxidant such as dichlorodicyanoquinone is employed to rearomatize the heterocyclic ring to produce (IIa). Substitution of an α-halonitrile for the α-haloketone in this process leads to compounds of the invention in which $R^2$ is amino; sustitution of an α-haloester leads to compounds in which $R^2$ is hydroxy. This hydroxy group may be converted to a halogen using standard

Scheme III

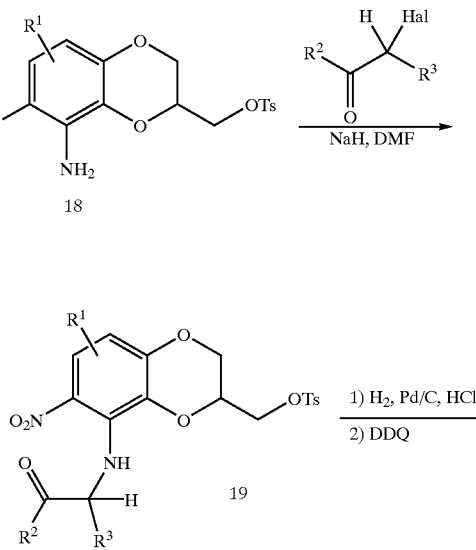

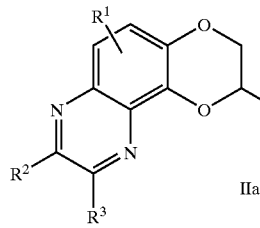

methods such as treatment with phosphoryl chloride or thionyl chloride and the halide may be used to prepare compounds of the invention in which $R^2$ is mono- or dialkylamino or alkoxy. Replacement of the tosylate with the appropriately substituted azaheterocycle as above gives the title compounds of the invention.

The guaiacols, catechols and azaheterocycles appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitrobenzene-sulfonate or tosylate (for the R enantiomer) in place of epihalohydrin or racemic glycidyl tosylate in the procedures above.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OHDPAT (dipropylamino-tetralin) from the 5-HT$_{1A}$ serotonin receptor following a modification of the procedure of Hall et al., J. Neurochem. 44, 1685 (1985) which utilizes CHO cells stably transfected with human 5-HT$_{1A}$ receptors. The 5-HT$_{1A}$ affinities for the compounds of the invention are reported below as $K_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OH DPAT. The test compound's maximum inhibitory effect is represented as the I$_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity KI (nM) | 5-HT1A Function IC$_{50}$ (nM) (I$_{max}$) |
|---|---|---|---|
| Example 1 | 0.50 | 17.72 | 270.5 (100) |
| Example 2 | 2.86 | 29.99 | 203.0 (100) |
| Example 3 | 1.19 | 15.28 | 332.0 (100) |
| Example 4 | 1.57 | 25.53 | 389.0 (100) |
| Example 5 | 9.50 | 99.18 | 1859.0 (98.0) |
| Example 6 | 14.00 | 264.30 | 2242.0 (100) |

Hence, the compounds of this invention are combined serotonin reuptake inhibitors/5-HT$_{1A}$ antagonists and are useful for the treatment of conditions related to or affected by the reuptake of serotonin and by the serotonin IA receptor, such as depression, (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addiction, sexual dysfunction (including premature ejaculation), and related illnesses. Moreover, the compounds of this invention have potent affinity for and antagonist activity at brain 5-HT$_{1A}$ serotonin receptors. Recent clinical trials employing drug mixtures (eg, fluoxetine and pindolol) have demonstrated a more rapid onset of antidepressant efficacy for a treatment combining SSRI activity and 5-HT$_{1A}$ antagonism (Blier and Bergeron, 1995; F. Artigas et. al., 1996; M. B. Tome et. al., 1997). The compounds of the invention are thus exceedingly interesting and useful for treating depressive illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein, means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

3-Allyloxy4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tic (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93–94° C.

INTERMEDIATE 2

2-Allyloxy-4-nitrophenol

To 1 L of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tic 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethylacetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

INTERMEDIATE 3

2-(2-Allyloxy4-nitrophenoxymethyl)-oxirane 20 g (0.50 mole) of 60% NaH/mineral oil was placed in a two liter flask and washed with 500 mL of hexane. One liter of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C.).

Elemental Analysis for: $C_{12}H_{13}NO_5$
Calc'd: C, 57.37; H, 5.21; N, 5.58
Found: C, 57.50; H, 5.21; N, 5.43

INTERMEDIATE 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$
Calc'd: C, 57.37; H, 5.21; N, 5.58
Found: C, 57.26; H, 5.20; N, 5.35

INTERMEDIATE 5

Toluene-4-sulfonic acid 8-allyl-7-nitro-2,3-dihydro-benzo(1,4)dioxin-2-ylmethyl ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$
Calc'd: C, 56.29; H, 4.72; N, 3.45
Found: C, 56.13; H, 4.58; N, 3.44

INTERMEDIATE 6

{7-Nitro-8-[-propenyl]-2,3-dihydro-1,4-benzodioxin-2-yl}methyl4-methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$
Calc'd: C, 56.29; H, 4.72; N, 3.45
Found: C, 56.12; H, 4.64; N, 3.39

INTERMEDIATE 7

(8-Formyl-7-nitro-2,3-dihydro-1,4-benzodioxin-2-yl) methyl 4-methylbenzenesulfonate {(2R)-7-Nitro-8-[1-propenyl]-2,3-dihydro-1,4-benzodioxin-2-yl}methyl 4-methylbenzenesulfonate (10.5 g, 25.9 mmole) dissolved in 400 mL of methylene chloride was treated with excess ozone at −78° C. Diisopropylethylamine (11.5 mL, 66.0 mmole) was then added dropwise over 30 min and the mixture allowed to come to room temperature and stir overnight under a nitrogen atmosphere. The mixture was then diluted to 600 mL with methylene chloride, washed three times with 100 mL portions of 2N HCl (aq), twice with 200 mL portions of saturated aqueous sodium bicarbonate and with 200 mL of saturated brine. The solution was dried over magnesium sulfate, filtered and concentrated in vacuum to a crude brown oil, which was column chromatographed on silica gel with 10% hexane/methylene chloride to give 7.52 g of the (R)-enantiomer of the title compound as a yellow solid. $^1$H-NMR (CDCl$_3$): doublet 7.8 δ (2 H); doublet 7.62 δ (1 H); doublet 7.4 δ (2 H); doublet 7.0 δ (1 H); multiplet 4.4–4.6 δ (2 H); multiplet 4.2 δ (3 H); singlet 2.4 δ (3 H).

INTERMEDIATE 8

6-Nitro-3-(toluene-4-sulfonyloxymethyl)-2,3-dihydro-benzo[1,4]dioxin-5-yl) carboxylic acid The oxidation reagent was prepared by dissolving 7.0 g (70 mmole) of chromium trioxide in 10 mL of water in a 50 mL beaker. The beaker was immersed in an ice bath and 6.1 mL (110 mmoles) of concentrated sulfuric acid added, followed by 20 mL additional water. The oxidant was added dropwise to a solution of (2R)-(8-formyl-7-nitro-2,3-dihydro-1,4-benzodioxin-2-yl)methyl 4-methylbenzenesulfonate (12.4 g, 30.6 mmole) dissolved in 100 mL of acetone and cooled in an ice bath. The mixture was stirred at room temperature for 3 hours after the addition was complete. Sodium bisulfite was then added in small portions until the brown color was gone. The mixture was diluted to 500 mL with water and extracted twice with 300 mL portions of ethyl acetate. The combined extracts were washed with 300 mL of water and with 300 mL of saturated brine, dried over sodium sulfate, filtered and evaporated to 13.4 g of the (R)-enantiomer of the title compound as a viscous yellow oil. $^1$H-NMR (CDCl$_3$): 2 superimposed doublets 7.8 δ (3 H); doublet 7.4 δ (2 H); doublet 7.0 δ (1 H); multiplet 4.55 δ (1 H); doublet 4.45 δ (1 H); multiplet 4.25 δ (3 H); singlet 2.4 δ (3 H).

INTERMEDIATE 9

Toluene-4-sulfonic acid 8-amino-7-nitro-2,3-dihydro-benzo(1,4)dioxin-2-ylmethyl ester To 7.0 g (17 mmole) of (S)-6-nitro-3-(toluene-4-sulfonyloxymethyl)-2,3-dihydro-benzo[1,4]dioxin-5-yl)

carboxylic acid in 250 mL of THF was added 9.4 g (34 mmole) of diphenylphosphoryl azide and 5.2 g (40 mmole) of diisopropyl-ethylamine and the mixture was refluxed under nitrogen for 24 hours. Water (3 mL) was added and the mixture refluxed under nitrogen overnight. The reaction was diluted to 600 mL with ethyl acetate and washed with 300 mL portions of 1 N HCl, saturated aqueous sodium bicarbonate and saturated brine. The mixture was then dried over sodium sulfate, filtered and concentrated in vacuum and the residue column chromatographed on silica gel with methylene chloride as eluant to give 4.1 g of the (R)-enantiomer of the title compound as a yellow solid (m.p. 155° C.).

Elemental Analysis for: $C_{16}H_{16}N_2O_7S$

Calc'd: C, 50.52; H, 4.24; N, 7.36

Found: C, 50.27; H, 3.99; N, 7.23

INTERMEDIATE 10

[7,8-Diamino-2,3-dihydro-1,4-benzodioxin-2-yl] methyl 4-methylbenzenesulfonate

Toluene-4-sulfonic acid (2R)-8-amino-7-nitro-2,3-dihydro-benzo(1,4)-dioxin-2-ylmethyl ester (4.1 g, 11 mmole) was dissolved in 200 mL of methanol to which 0.50 g of 10% palladium on carbon had been added. 4 N isopropanol HCl (10 mL) was then added and the mixture treated with 60 psi of hydrogen on a Parr apparatus overnight. The mixture was filtered through celite and concentrated in vacuum to give 4.6 g of the (R)-enantiomer of the title compound as a pink solid (m.p. 178–180° C.).

Elemental Analysis for: $C_{16}H_{18}N_2O_5S \cdot 2$ HCl

Calc'd: C, 45.40; H, 4.76; N, 6.62

Found: C, 45.06; H, 4.63; N, 6.47

INTERMEDIATE 11

2,3-Dihydro[1,4]dioxino[2,3-f]quinoxalin-2-ylmethyl 4-methylbenzenesulfonate

To a solution of [(2R)-7,8-diamino-2,3-dihydro-1,4-benzodioxin-2-yl]methyl 4-methylbenzenesulfonate (2.226 g, 5.258 mmole) in water (50 mL) was added a solution of glyoxal trimeric dihydrate (1.104 g, 5.258 mmole) in ethyl alcohol (50 mL) and the reaction mixture was heated at 60° C. for 3 hours. The reaction mixture was allowed to cool to room temperature and was diluted with aqueous sodium hydrogen carbonate (250 mL) and extracted with ethyl acetate (2×100 mL). The combined organic extracts were washed with water (100 mL), aqueous sodium chloride (100 mL), dried (magnesium sulfate) and the solvent was removed in vacuo to give a crude solid. Purification by flash column chromatography (silica, ethyl acetate:hexanes 7:3) gave 1.135 g (58%) of the (R)-enantiomer of the title compound as a brown crystalline solid. $R_f$=0.27 (silica, ethyl acetate:hexanes 3:2); mp 124–127° C.

Elemental Analysis for: $C_{18}H_{16}N_2O_5S$ 0.2 $H_2O$

Calc'd: C, 57.50; H, 4.39; N, 7.45

Found: C, 57.27; H, 4.37; N, 7.04

EXAMPLE 1

2-{[4-(5-Fluoro-1H-indol-3-yl)-3,6-dihydro-1(2H)-pyridinyl]methyl}-2,3-dihydro[1,4]dioxino[2,3f] quinoxaline To a solution of (2R)-2,3-dihydro[1,4]dioxino[2,3-f] quinoxalin-2-ylmethyl 4-methylbenzenesulfonate (0.462 g, 1.241 mmole) in methyl sulfoxide (25 mL) was added 5-fluoro-3-(1,2,3,6-tetrahydro-4-pyridinyl)-1H-indole (1.073 g, 4.962 mmole) and the reaction mixture was heated to 80° C. for 12 hours. The reaction mixture was allowed to cool to room temperature and was diluted with ethyl acetate (250 mL), washed with water (2×100 mL), aqueous sodium chloride (100 mL), dried (magnesium sulfate) and the solvent was removed in vacuo to give a crude solid. Purification by flash column chromatography (silica, methanol:ethyl acetate 1:9) followed by recrystallization from ethanol provided 0.382 g (74%) of the (S)-enantiomer of the title compound as a tan solid. $R_f$=0.37 (silica, methanol:ethyl acetate 1:9); mp>200° C. dec.

Elemental Analysis for: $C_{24}H_{21}FN_4O_2 \cdot 0.2\ H_2O$

Calc'd: C, 68.63; H, 5.14; N, 13.34

Found: C, 68.61; H, 5.35; N, 13.16

EXAMPLE 2

2-{[(4-(1H-Indol-3-yl)-3,6-dihydro-1(2H)-pyridinyl] methyl}-2,3-dihydro[1,4]dioxino[2,3-f]quinoxaline To a solution of (2R)-2,3-dihydro[1,4]dioxino[2,3-f] quinoxalin-2-ylmethyl 4-methylbenzenesulfonate (0.300 g, 0.856 mmole) in methyl sulfoxide (20 mL) was added 3-(1,2,3,6-tetrahydro-4-pyridinyl)-1H-indole (0.639 g, 3.222 mmole) and the reaction mixture was heated to 80° C. for 12 hours. The reaction mixture was allowed to cool to room temperature and was diluted with ethyl acetate (200 mL), washed with water (2×100 mL), aqueous sodium chloride (100 mL), dried (magnesium sulfate) and the solvent was removed in vacuo to give a crude solid. Purification by flash column chromatography (silica, methanol:ethyl acetate 1:9) followed by recrystallization from ethanol provided 0.248 g (77%) of the (S)-enantiomer of the title compound as a pale yellow solid. $R_f$=0.36 (silica, methanol:ethyl acetate 1:9); mp >220° C. dec.

Elemental Analysis for: $C_{24}H_{22}N_4O_2 \cdot 0.25\ H_2O$

Calc'd: C, 71.54; H, 5.63; N, 13.90

Found: C, 71.36; H, 5.63; N, 13.62

INTERMEDIATE 12

8,9-Dimethyl-2,3-dihudro[1,4]dioxino[2,3-f] quinoxalin-2-ylmethyl 4-methylbenzenesulfonate To a solution of [(2R)-7,8-diamino-2,3-dihydro-1,4-benzodioxin-2-yl]-methyl 4-methylbenzenesulfonate (2.170 g, 5.126 mmole) in water (50 mL) was added a solution of 2,3-butanedione (0.552 g, 6.408 mmole) in ethyl alcohol (50 mL) and the reaction mixture was heated at 60° C. for 3 hours. The reaction mixture was allowed to cool to room temperature and was diluted with aqueous sodium hydrogen carbonate (250 mL) and extracted with ethyl acetate (2×100 mL). The combined organic extracts were washed with water (100 mL), aqueous sodium chloride (100 mL), dried (magnesium sulfate) and the solvent was removed in vacuo to give a crude solid. Purification by flash column chromatography (silica, ethyl acetate:hexanes 7:3) gave 1.525 g (74%) of the (R)-enantiomer of the title compound as a white crystalline solid. $R_f$=0.50 (silica, ethyl acetate:hexanes 7:3); mp 153–155° C.

Elemental Analysis for: $C_{20}H_{20}N_2O_5S \cdot 0.21\ C_4H_8O_2$

Calc'd: C, 59.75; H, 5.22; N, 6.69

Found: C, 59.36; H, 5.02; N, 6.69

EXAMPLE 3

2-{[4-(1H-Indol-3-yl)-3,6-dihydro-1(2H)-pyridinyl] methyl}-8,9-dimethyl-2,3-dihydro[1,4]dioxino[2,3-f] quinoxaline To a solution of [(2R)-8,9-dimethyl-2,3-dihydro[1,4] dioxino[2,3f]-quinoxalin-2-yl]methyl 4-methylbenzenesulfonate (0.400 g, 1.000 mmole) in methyl sulfoxide (20 mL) was added 3-(1,2,3,6-tetrahydro-4-pyridinyl)-1H-indole (0.495 g, 2.497 mmole) and the reaction mixture was heated to 80° C. for 12 hours. The reaction mixture was allowed to cool to room temperature and was diluted with ethyl acetate (250 mL), washed with water (2×100 mL), aqueous sodium chloride (100 mL), dried (magnesium sulfate) and the solvent was removed in vacuo to give a crude solid. Purification by flash column chromatography (silica, methanol:ethyl acetate 1:9) followed by recrystallization from ethanol provided 0.262 g (62%) of the (S)-enantiomer of the title compound as a pale yellow solid. $R_f$=0.32 (silica, methanol:ethyl acetate 1:9); mp 153–155° C.

Elemental Analysis for: $C_{26}H_{26}N_4O_2 \cdot 0.2\ H_2O$

Calc'd: C, 72.60; H, 6.19; N, 13.03

Found: C, 72.39; H, 6.15; N, 12.83

EXAMPLE 4

2-{[4-(5-Fluoro-1H-indol-3-yl)-3,6-dihydro-1(2H)-pyridinyilmethyl}-8,9-dimethyl-2,3-dihydro[1,4]dioxino[2,3-f]quinoxaline To a solution of [(2R)-8,9-dimethyl-2,3-dihydro[1,4]dioxino[2,3-f]-quinoxalin-2-yl]methyl 4-methylbenzenesulfonate (0.400 g, 1.000 mmole) in methyl sulfoxide (20 mL) was added 5-fluoro-3-(1,2,3,6-tetrahydro-4-pyridinyl)-1H-indole (0.540 g, 2.497 mmole) and the reaction mixture was heated to 80° C. for 12 hours. The reaction mixture was allowed to cool to room temperature and was diluted with ethyl acetate (250 mL), washed with water (2×100 mL), aqueous sodium chloride (100 mL), dried (magnesium sulfate) and the solvent was removed in vacuo to give a crude solid. Purification by flash column chromatography (silica, methanol:ethyl acetate 1:9) followed by recrystallization from ethanol provided 0.239 g (54%) of the (S)-enantiomer of the title compound as a pale yellow solid. $R_f$=0.35 (silica, methanol:ethyl acetate 1:9); mp 138–141° C.

Elemental Analysis for: $C_{26}H_{25}FN_4O_2 \cdot H_2O$

Calc'd: C, 67.37; H, 6.09; N, 12.09

Found: C, 66.96; H, 5.95; N, 11.85

INTERMEDIATE 13

8,9-Diethyl-2,3-dihydro[1,4]dioxino[2,3-f]quinoxalin-2-ylmethyl 4-methylbenzenesulfonate To a solution of [(2R)-7,8-diamino-2,3-dihydro-1,4-benzodioxin-2-yl]-methyl 4-methylbenzenesulfonate (2.226 g, 5.258 mmole) in water (50 mL) was added a solution of 3,4-hexanedione (0.750 g, 6.572 mmole) in ethyl alcohol (50 mL) and the reaction mixture was heated at 60° C. for 3 hours. The reaction mixture was allowed to cool to room temperature and was diluted with aqueous sodium hydrogen carbonate (250 mL) and extracted with ethyl acetate (2×100 mL). The combined organic extracts were washed with water (100 mL), aqueous sodium chloride (100 mL), dried (magnesium sulfate) and the solvent was removed in vacuo to give a crude solid. Purification by flash column chromatography (silica, ethyl acetate:hexanes 7:3) gave 1.796 g (80%) of the (R)-enantiomer of the title compound as a tan crystalline solid. $R_f$=0.85 (silica, ethyl acetate:hexanes 7:3); mp 132–135° C.

Elemental Analysis for: $C_{22}H_{24}N_2O_5S \cdot 0.1\ H_2O$

Calc'd: C, 61.41; H, 5.67; N, 6.51

Found: C, 61.21; H, 5.67; N, 6.43

EXAMPLE 5

8,9-Diethyl-2-{[4-(1H-indol-3-yl)-3,6-dihydro-1(2H)-pyridinyl]methyl}-2,3-dihydro[1,4]dioxino[2,3-t]quinoxaline To a solution of (2R)-8,9-diethyl-2,3-dihydro[1,4]dioxino[2,3-f]-quinoxalin-2-ylmethyl 4-methylbenzenesulfonate (0.300 g, 0.700 mmole) in methyl sulfoxide (20 mL) was added 3-(1,2,3,6-tetrahydro-4-pyridinyl)-1H-indole (0.555 g, 2.800 mmole) and the reaction mixture was heated to 80° C. for 12 hours. The reaction mixture was allowed to cool to room temperature and was diluted with ethyl acetate (250 mL), washed with water (2×100 mL), aqueous sodium chloride (100 mL), dried (magnesium sulfate) and the solvent was removed in vacuo to give a crude solid. Purification by flash column chromatography (silica, methanol:ethyl acetate 1:9) followed by recrystallization from ethanol provided 0.184 g (58%) of the (S)-enantiomer of the title compound as a yellow crystalline solid. $R_f$=0.41 (silica, methanol:ethyl acetate 1:9); mp >120° C. dec.

Elemental Analysis for: $C_{28}H_{30}N_4O_2 \cdot 0.7\ H_2O$

Calc'd: C, 71.99; H, 6.77; N, 11.99

Found: C, 71.85; H, 6.91; N, 11.96

EXAMPLE 6

8,9-Diethyl-2-{[4-(5-fluoro-1H-indol-3-yl)-3,6-dihydro-1(2H)-pyridinyl]methyl}-2,3-dihydro[1,4]dioxino[2,3-f]quinoxaline To a solution of (2R)-8,9-diethyl-2,3-dihydro[1,4]dioxino[2,3-f]-quinoxalin-2-ylmethyl 4-methylbenzenesulfonate (0.300 g, 0.700 mmole) in methyl sulfoxide (20 mL) was added 5-fluoro-3-(1,2,3,6-tetrahydro-4-pyridinyl)-1H-indole (0.606 g, 2.800 mmole) and the reaction mixture was heated to 80° C. for 12 hours. The reaction mixture was allowed to cool to room temperature and was diluted with ethyl acetate (250 mL), washed with water (2×100 mL), aqueous sodium chloride (100 mL), dried (magnesium sulfate) and the solvent was removed in vacuo to give a crude solid. Purification by flash column chromatography (silica, methanol:ethyl acetate 1:9) followed by recrystallization from ethanol provided 0.161 g (49%) of the (S)-enantiomer of the title compound as a yellow crystalline solid. Rf =0.38 (silica, methanol:ethyl acetate 1:9); mp>120° C. dec.

Elemental Analysis for: $C_{28}H_{29}FN_4O_2 \cdot H_2O$

Calc'd: C, 68.55; H, 6.37; N, 11.42

Found: C, 68.33; H, 6.43; N, 11.27

What is claimed is:

1. A compound of formula I

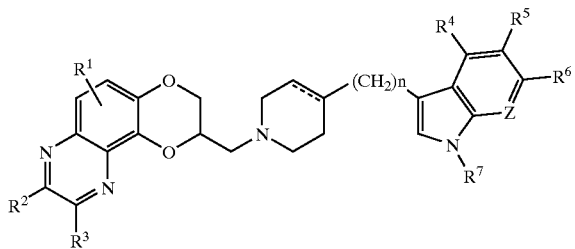

wherein $R^1$, $R^4$, $R^5$, $R^6$ and $R^8$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ and $R^3$ are, independently, hydrogen, alkyl of 1 to 6 carbon atoms, halogen, hydroxy, cyano or amino;

$R^7$ is hydrogen or alkyl of 1 to 6 carbon atoms;

the dotted line represents an optional double bond;

Z is $CR^8$ or N; and n is an integer 0, 1 or 2;

or a pharmaceutically acceptable salt thereof.

2. A compound of claim 1 wherein $R^1$ is hydrogen, hydroxy, halo, cyano, trifluoromethyl, alkyl of one to six carbon atoms or alkoxy of one to six carbon atoms.

3. A compound of claim 1 wherein $R^2$ is hydrogen, alkyl of one to six carbon atoms, amino, mono- or di-alkylamino in which each alkyl group has one to six carbon atoms.

4. A compound of claim 1 wherein $R^3$ is hydrogen or alkyl of one to six carbon atoms.

5. A compound of claim 1 wherein $R^2$ and $R^3$ are the same.

6. A compound of claim 1 wherein $R^4$, $R^5$ and $R^6$ are independently selected from hydrogen, hydroxy, halogen, cyano, carboxamido, alkyl of one to six carbon atoms, and alkoxy of one to six carbon atoms.

7. A compound of claim 1 wherein n is an integer 0.

8. A compound of claim 1 in which $R^1$ is hydrogen, hydroxy, halo, cyano, trifluoromethyl, alkyl of one to six carbon atoms or alkoxy of one to six carbon atoms; $R^2$ is hydrogen, alkyl of one to six carbon atoms, amino, mono- or di-alkylamino in which each alkyl group has one to six carbon atoms; $R^3$ is hydrogen or alkyl of one to six carbon atoms; $R^4$, $R^5$ and $R^6$ are independently selected from hydrogen, hydroxy, halo, cyano, carboxamido, alkyl of one to six carbon atoms, and alkoxy of one to six carbon atoms; n is an integer 0 or 1; or a pharmaceutically acceptable salt thereof.

9. A compound of claim 8 wherein when Z is $CR^8$ and $R^8$ is hydrogen, hydroxy, halo, cyano, carboxamido, alkyl of one to six carbon atom, or alkoxy of one to six carbon atoms.

10. A compound of claim 1 in which $R^1$ is hydrogen, hydroxy, halo, cyano, trifluoromethyl, alkyl of one to six carbon atoms or alkoxy of one to six carbon atoms; $R^2$ and $R^3$ are the same and are hydrogen or alkyl of one to six carbon atoms, $R^4$, $R^5$ and $R^6$ are independently selected from hydrogen, halogen and cyano, $R^7$ is hydrogen, n is 0 and the dotted line represents a double bond; or a pharmaceutically acceptable salt thereof.

11. A compound of claim 10 wherein when Z is $CR^8$ and $R^8$ is hydrogen, halogen or cyano.

12. A compound of claim 1 which is the S stereoisomer.

13. The compound of claim 1 which is 2-{[4-(5-fluoro-1H-indol-3-yl)-3,6-dihydro-1(2H)-pyridinyl]methyl}-2,3-dihydro[1,4]dioxino[2,3-f]quinoxaline or a pharmaceutically acceptable salt thereof.

14. The compound of claim 1 which is 2-{[4-(1H-indol-3-yl)-3,6-dihydro-1(2H)-pyridinyl]methyl}-2,3-dihydro[1,4]dioxino[2,3-f]quinoxaline or a pharmaceutically acceptable salt thereof.

15. The compound of claim 1 which is 2-{[4-(1H-indol-3-yl)-3,6-dihydro-1(2H)-pyridinyl]methyl}-8,9-dimethyl-2,3-dihydro[1,4]dioxino[2,3-f]quinoxaline or a pharmaceutically acceptable salt thereof.

16. The compound of claim 1 which is 2-{[4-(5-fluoro-1H-indol-3-yl)-3,6-dihydro-1(2H)-pyridinyl]methyl}-8,9-dimethyl-2,3-dihydro[1,4]dioxino[2,3-f]-quinoxaline or a pharmaceutically acceptable salt thereof.

17. The compound of claim 1 which is 8,9-diethyl-2-{[4-(1H-indol-3-yl)-3,6-dihydro-1(2H)-pyridinyl]methyl}-2,3-dihydro[1,4]dioxino[2,3-f]quinoxaline or a pharmaceutically acceptable salt thereof.

18. The compound of claim 1 which is 8,9-diethyl-2-{[4-(5-fluoro-1H-indol-3-yl)-3,6-dihydro-1(2H)-pyridinyl]methyl}-2,3-dihydro[1,4]dioxino[2,3-f]quinoxaline or a pharmaceutically acceptable salt thereof.

19. A compound of the formula

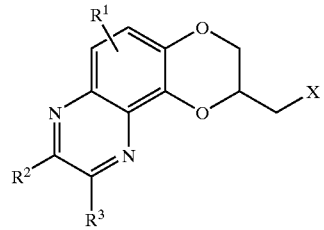

wherein $R^1$ is hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ and $R^3$ are independently selected from hydrogen, alkyl of 1 to 6 carbon atoms, halogen, hydroxy, cyano or amino;

X is hydroxy, halogen, alkylsulfonate of 1 to 6 carbon atoms, trifluoromethanesulfonate or benzenesulfonate, in which the benzene ring is optionally substituted with halogen, nitro, trifluoromethyl, cyano, alkyl of 1 to 6 carbon atoms or alkoxy of 1 to 6 carbon atoms.

20. A compound of claim 19 which is:

2,3-Dihydro[1,4]dioxino[2,3-f]quinoxalin-2-ylmethyl 4-methylbenzene-sulfonate;

8,9-dimethyl-2,3-dihydro[1,4]dioxino[2,3-f]quinoxalin-2-yl]methyl 4-methyl-benzenesulfonate; or 8,9-diethyl-2,3-dihydro[1,4]dioxino[2,3-f]-quinoxalin-2-ylmethyl 4-methyl-benzenesulfonate.

21. A method of treating a subject suffering from a condition selected from the group consisting of depression, anxiety, panic disorder, post-traumatic stress disorder, premenstrual dysphoric disorder, attention deficit disorder, obsessive compulsive disorder, social anxiety disorder, generalized anxiety disorder, obesity, eating disorders, vasomotor flushing, cocaine and alcohol addiction, and sexual dysfunction, which comprises providing to the subject suffering from said condition, a therapeutically effective amount of a compound of formula I

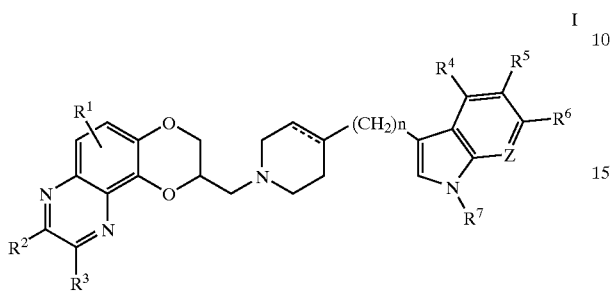

wherein
$R^1$, $R^4$, $R^5$, $R^6$ and $R^8$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ and $R^3$ are, independently, hydrogen, alkyl of 1 to 6 carbon atoms, halogen, hydroxy, cyano or amino;

$R^7$ is hydrogen or alkyl of 1 to 6 carbon atoms;

the dotted line represents an optional double bond;

Z is $CR^8$ or N; and n is an integer 0, 1 or 2;

or a pharmaceutically acceptable salt thereof.

22. The method of claim 19 wherein the condition is depression.

23. The method of claim 19 wherein the condition is obsessive compulsive disorder, panic attacks, generalized anxiety disorder, or social anxiety disorder.

24. The method of claim 19 wherein the subject is a human.

25. A pharmaceutical composition comprising a compound of formula I

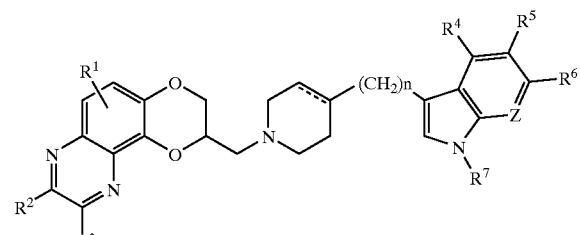

wherein $R^1$, $R^4$, $R^5$, $R^6$ and $R^8$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ and $R^3$ are, independently, hydrogen, alkyl of 1 to 6 carbon atoms, halogen, hydroxy, cyano or amino;

$R^7$ is hydrogen or alkyl of 1 to 6 carbon atoms;

the dotted line represents an optional double bond;

Z is $CR^8$ or N; and n is an integer 0, 1 or 2;

or a pharmaceutically acceptable salt thereof and a pharmaceutically acceptable carrier or excipient.

* * * * *

UNITED STATES PATENT AND TRADEMARK OFFICE
CERTIFICATE OF CORRECTION

PATENT NO.    : 6,617,327 B2
DATED         : September 9, 2003
INVENTOR(S)   : Jonathan L. Gross and Gary P. Stack It is certified that error appears in the above-identified patent and that said Letters Patent is hereby corrected as shown below:

Column 3,
Line 27, please delete "coresonding" and insert -- corresponding -- therefor.

Column 4,
Line 51, please delete "Schemes I-Ill." and insert -- Schemes I-III -- therefor.

Column 7,
Lines 58-59, please delete "Scheme Ill." and insert -- Scheme III. -- therefor.

Column 8,
Line 40, please delete "sustitution" and insert -- substitution -- therefor.

Column 10,
Line 4, please delete "5-HT1A" and insert -- $5\text{-}HT_{1A}$ -- therefor.
Line 16, please delete "IA" and insert -- 1A -- therefor.

Column 12,
Line 15, please delete "3-Allyloxy4-methoxynitrobenzene" and insert -- 3-Alloyloxy-4-methoxynitrobenzene -- therefor.
Lines 21 and 40, please delete "tic" and insert -- tlc -- therefor.

Column 13,
Line 11, please delete "tic" and insert -- tlc -- therefor.
Line 64, please delete "{7-Nitro-8-[-propenyl]-2,3-dihydro-1,4-" and insert -- {7-Nitro-8-[1-propenyl]-2,3-dihydro-1,4- -- therefore.
Line 65, please delete "benzodioxin-2-yl}methyl4-methylbenzenesulfonate" and insert -- benzodioxin-2-yl}methyl 4-methylbenzenesulfonate -- therefor.

Column 14
Line 34, please delete "7.62 8 (1 H);" and insert -- 7.62 δ (1 H); -- therefor.
Line 35, please delete "4.4-4.6 8 (2 H);" and insert -- 4.4-4.6 δ (2 H); -- therefor.

Column 15,
Line 7, please delete "HCI," and insert -- HCl, -- therefor.
Line 56, please delete "$C_{18}H_{16}N_2O_5S$ 0.2 $H_2O$" and insert -- $C_{18}H_{16}N_2O_5S \cdot 0.2\ H_2O$ -- therefor.
Line 63, please delete "pyridinyl]methyl}-2,3-dihydro[1,4]dioxino[2,3f]" and insert -- pyridinyl]methyl}-2,3-dihydro[1,4]dioxino[2,3-f] -- therefor.

UNITED STATES PATENT AND TRADEMARK OFFICE
CERTIFICATE OF CORRECTION

PATENT NO. : 6,617,327 B2
DATED : September 9, 2003
INVENTOR(S) : Jonathan L. Gross and Gary P. Stack It is certified that error appears in the above-identified patent and that said Letters Patent is hereby corrected as shown below:

Column 16,
Line 40, please delete "8,9-Dimethyl-2,3-dihudro[1,4]dioxino[2,3-f]" and insert -- 8,9-Dimethyl-2,3-dihydro[1,4]dioxino[2,3-f] -- therefor.

Column 17,
Line 22, please delete "pyridinyilmethyl}-8,9-dimethyl-2,3-dihydro[1,4]" and insert -- pyridinyl]methyl}-8,9-dimethyl-2,3-dihydro[1,4] -- therefor.

Column 18,
Line 6, please delete "3-t]quinoxaline" and insert -- 3-f]quinoxaline -- therefor.
Line 48, please delete "II-indole" and insert -- H-indole -- therefor.

Column 21,
Line 3, after "social anxiety disorder," insert -- and -- therefor.
Lines 4-6, after "anxiety disorder," please delete "obesity, eating disorders, vasomotor flushing, cocaine and alcohol addition, and sexual dysfunction,".

Signed and Sealed this

Third Day of May, 2005

JON W. DUDAS
*Director of the United States Patent and Trademark Office*